US012790215B2

(12) United States Patent
Schmidt et al.

(10) Patent No.: US 12,790,215 B2
(45) Date of Patent: Nov. 10, 2026

(54) METHOD FOR PREPARING IMIDE SALTS CONTAINING A FLUOROSULFONYL GROUP

(71) Applicant: Arkema France, Colombes (FR)

(72) Inventors: Grégory Schmidt, Pierre-Benite (FR); Dominique Deur-Bert, Pierre-Benite (FR); Rémy Teissier, Pierre-Benite (FR)

(73) Assignee: Arkema France, Puteaux (FR)

( * ) Notice: Subject to any disclaimer, the term of this patent is extended or adjusted under 35 U.S.C. 154(b) by 1057 days.

(21) Appl. No.: 17/059,574

(22) PCT Filed: May 28, 2019

(86) PCT No.: PCT/FR2019/051237

§ 371 (c)(1),
(2) Date: Nov. 30, 2020

(87) PCT Pub. No.: WO2019/229359

PCT Pub. Date: Dec. 5, 2019

(65) Prior Publication Data

US 2021/0214220 A1 Jul. 15, 2021

(30) Foreign Application Priority Data

Jun. 1, 2018 (FR) ...................................... 1854763

(51) Int. Cl.

*C01B 21/086* (2006.01)
*C07C 303/40* (2006.01)
*C07C 303/44* (2006.01)
*H01M 10/0525* (2010.01)
*H01M 10/0568* (2010.01)

(52) U.S. Cl.

CPC .......... *C01B 21/086* (2013.01); *C07C 303/40* (2013.01); *C07C 303/44* (2013.01); *H01M 10/0525* (2013.01); *H01M 10/0568* (2013.01); *C01P 2006/40* (2013.01); *H01M 2300/0025* (2013.01)

(58) Field of Classification Search

CPC ... C07C 303/40; C07C 303/44; C07C 311/48; C01B 21/086

See application file for complete search history.

(56) References Cited

U.S. PATENT DOCUMENTS 6,103,131 A 8/2000 McNeel et al.
6,198,011 B1 3/2001 Chambers et al.
7,919,629 B2 4/2011 Michot
8,062,606 B2 11/2011 Devic
8,377,406 B1 * 2/2013 Singh .................. H01M 10/052 423/617

(Continued)

FOREIGN PATENT DOCUMENTS

AU 1998086626 A1 4/1999
CA 2 527 802 A1 6/2007

(Continued)

OTHER PUBLICATIONS

Machine translation of JP2016204218A, Dec. 8, 2016; pp. 1-7 (Year: 2016).*

Machine translation of WO2016184176A1, Nov. 24, 2016; pp. 1-7 (Year: 2016).*

Han, H-B. et al. "Efficient Preparation of (Fluorosulfonyl)(pentafluoroethanesulfonyl)imide and Its Alkali Salts" Chem. Lett. 2010, 39, 472474 and supporting information pp. 1-6 (Year: 2010).*

Beran (Beran, M. et al. A new route to the syntheses of N-(fluorosulfuryl)sulfonamide salts: Crystal structure of Ph4P+ [CF3S02NS02F]-Polyhedron 29 (2010) 991-994) (Year: 2010).*

Han, et al., "Lithium bis(fluorosulfonyl)imide (LiFSI) as conducting salt for nonaqueous liquid electrolytes for lithium-ion batteries: Physicochemical and electrochemical properties", Journal of Power Sources, 2011 (month unknown), vol. 196, No. 7, pp. 3623-3632.

International Search Report (PCT/ISA/210) and translation and Written Opinion (PCT/ISA/237) mailed on Sep. 17, 2019, by the European Patent Office as the International Searching Authority for International Application No. PCT/FR2019/051237.

Yang, D."Safety Principle, Design and Test of Lithium Ion Battery" University of Electronic Science and Technology Press, May 31, 2012, 16 pages.

Han, C. et al. "Production Technology of Fine Inorganic Chemicals" Science and Technology Literature Publishing House, Aug. 2008, 18 pages.

Office Action (The Decision of Final Rejection of the Application) issued on Jun. 28, 2023, by the China National Intellectual Property Administration in corresponding Chinese Patent Application No. 2019800370635.5, English Translation only (14 pages).

Ueda, S. et al., Various Properties of Nickel and its Shaping, Treating, Denki Seiko, vol. 36, No. 1, 1965, pp. 30-47, (with a Statement of Relevancy).

(Continued)

*Primary Examiner* — Medhanit W Bahta
(74) *Attorney, Agent, or Firm* — Buchanan Ingersoll & Rooney PC

(57) ABSTRACT

The present invention concerns a method for preparing a compound of the following formula (III): $R_2$—($SO_2$)—NM—($SO_2$)—F (III) in which $R_2$ represents one of the following radicals: F, $CF_3$, $CHF_2$, $CH_2F$, $C_2HF_4$, $C_2H_2F_3$, $C_2H_3F_2$, $C_2F$, $C_3F_7$, $C_3H_4F_3$, $C_3HF_6$, $C_4F_9$, $C_4H_2F_7$, $C_4H_4F$, $CF_{11}$, $C_6F_{13}$, $C_7F_1$, $C_8F_{17}$ or $C_9F_{19}$. M represents a monovalent or divalent cation; the method comprising: —a step b) of fluorinating a compound of the following formula (I): $R_1$—($SO_2$)—NH—($SO_2$)—Cl (I) in which R represents one of the following radicals: Cl, F, $CF_3$, $CHF_2$, $CH_2F$, $C_2HF_4$, $C_2H_2F_3$, $C_2H_3F_2$, $C_2F$, $C_3F_7$, $C_3H_4F_3$, $C_3HF_6$, $C_4F_9$, $C_4H_2F_7$, $C_4H_4F$, $CF_{11}$, $C_6F_{13}$, $C_7F_{15}$, $C_8F_{17}$ or $C_9F_{19}$, R preferably representing Cl; with at least one fluorinating agent; 2—a step c) of distilling the composition obtained in step b).

11 Claims, No Drawings

(56) References Cited

U.S. PATENT DOCUMENTS

| | | | | |
|---|---|---|---|---|
| 8,722,005 | B1 | 5/2014 | Poshusta et al. | |
| 9,546,136 | B2 | 1/2017 | Schnider et al. | |
| 9,725,318 | B2 | 8/2017 | Audureau et al. | |
| 10,122,038 | B2 | 11/2018 | Yoshida et al. | |
| 2011/0034716 | A1* | 2/2011 | Okumura | C07C 303/40 556/69 |
| 2012/0041233 | A1 | 2/2012 | Sato et al. | |
| 2013/0068991 | A1 | 3/2013 | Sato et al. | |
| 2013/0323155 | A1 | 12/2013 | Tsubokura et al. | |
| 2013/0331609 | A1 | 12/2013 | Tsubokura et al. | |
| 2014/0075746 | A1 | 3/2014 | Schmidt | |
| 2015/0126778 | A1* | 5/2015 | Poshusta | C07C 303/40 564/82 |
| 2015/0246812 | A1 | 9/2015 | Audureau et al. | |
| 2016/0016797 | A1 | 1/2016 | Maekawa et al. | |
| 2016/0176794 | A1 | 6/2016 | Su | |
| 2016/0308247 | A1 | 10/2016 | Buisine | |
| 2017/0047607 | A1 | 2/2017 | Schmidt et al. | |
| 2018/0141901 | A1 | 5/2018 | Schnider et al. | |
| 2018/0362343 | A1 | 12/2018 | Hormes et al. | |
| 2018/0370799 | A1 | 12/2018 | Lim | |
| 2019/0152792 | A1 | 5/2019 | Yamada et al. | |
| 2019/0276311 | A1 | 9/2019 | Itayama et al. | |
| 2019/0292053 | A1 | 9/2019 | Schmidt et al. | |
| 2021/0050625 | A1 | 2/2021 | Nozaki et al. | |
| 2021/0122634 | A1 | 4/2021 | Leduc et al. | |
| 2021/0188638 | A1 | 6/2021 | Leduc et al. | |
| 2021/0214219 | A1 | 7/2021 | Leduc et al. | |
| 2021/0214239 | A1 | 7/2021 | Leduc et al. | |
| 2021/0221685 | A1 | 7/2021 | Schmidt et al. | |
| 2023/0312344 | A1 | 10/2023 | Schmidt et al. | |

FOREIGN PATENT DOCUMENTS

| | | | | |
|---|---|---|---|---|
| CN | 102405189 | A | 4/2012 | |
| CN | 103384641 | A | 11/2013 | |
| CN | 103391896 | A | 11/2013 | |
| CN | 105121335 | A | 12/2015 | |
| CN | 105392736 | A | 3/2016 | |
| CN | 105916805 | A | 8/2016 | |
| CN | 107055493 | A | 8/2017 | |
| CN | 107635916 | A | 1/2018 | |
| CN | 107673319 | A | 2/2018 | |
| CN | 110467163 | B | 5/2021 | |
| EP | 2 505 551 | A1 | 10/2012 | |
| EP | 2 578 533 | A1 | 4/2013 | |
| EP | 2 660 196 | A1 | 11/2013 | |
| JP | 2008169448 | A | 7/2008 | |
| JP | 2015531744 | A | 11/2015 | |
| JP | 2016-052982 | A | 4/2016 | |
| JP | 2016 204054 | A | 12/2016 | |
| JP | 2016204218 | A * | 12/2016 | |
| JP | 2016540040 | A | 12/2016 | |
| JP | 2017-503740 | A | 2/2017 | |
| JP | 2017514779 | A | 6/2017 | |
| JP | 2018052760 | A | 4/2018 | |
| JP | 2018055882 | A | 4/2018 | |
| JP | 2018520981 | A | 8/2018 | |
| JP | 6691740 | B2 | 4/2020 | |
| JP | 2021526499 | A | 10/2021 | |
| KR | 10-0982605 | B1 | 9/2010 | |
| KR | 101718292 | B1 | 3/2017 | |
| WO | 2006/100317 | A1 | 9/2006 | |
| WO | WO 2009/123328 | A1 | 10/2009 | |
| WO | 2011/065502 | A1 | 6/2011 | |
| WO | 2011/149095 | A1 | 12/2011 | |
| WO | 2012113778 | A1 | 8/2012 | |
| WO | 2014/035464 | A1 | 3/2014 | |
| WO | WO 2014/080120 | A1 | 5/2014 | |
| WO | 2014/148258 | A1 | 9/2014 | |
| WO | 2015/004220 | A1 | 1/2015 | |
| WO | 2015012897 | A1 | 1/2015 | |
| WO | 2015/066660 | A1 | 5/2015 | |
| WO | WO 2015/082532 | A1 | 6/2015 | |
| WO | WO 2015/158979 | A1 | 10/2015 | |
| WO | 2016177765 | A1 | 11/2016 | |
| WO | WO-2016184176 | A1 * | 11/2016 | C01B 21/086 |
| WO | WO 2017/090877 | A1 | 6/2017 | |
| WO | 2017/169874 | A1 | 10/2017 | |
| WO | 2017/204303 | A1 | 11/2017 | |
| WO | WO 2017/204225 | A1 | 11/2017 | |
| WO | WO 2018/104675 | A1 | 6/2018 | |
| WO | WO 2019/224470 | A1 | 11/2019 | |

OTHER PUBLICATIONS

Office Action (Notice of Reasons for Refusal) issued on May 23, 2023, by the Japanese Patent Office in corresponding Japanese Patent Application No. 2020-566239, and an English Translation of the Office Action. (12 pages).

International Search Report (with English translation) and Written Opinion, mailed Aug. 2, 2019 in PCT/FR2019/051244, 11 pages, European Patent Office, Rijswijk, NL.

Office Action mailed Dec. 27, 2021 in CN Application No. 201980035233.6, and English-language translation, China National Intellectual Property Administration, Beijing, CN, 18 pages.

Office Action mailed Jan. 13, 2022 in CN 201980037096.X, and English-language translation, The State Intellectual Property Office of People's Republic of China, Beijing, CN, 34 pages.

Xu, Panming, et al., "Practical Metal Material Analysis Method," 2nd Edition, May 2015, p. 435, ISBN 978-7-312-02800-7, China University of Science and Technology Press, CN (3 pages).

Beijing Architectural Decoration Industry Association, et al, "Quality Inspection and Evaluation Manual of Advanced Building Decoration Engineering," Oct. 1998, p. 12, ISBN 7-112-03505-8, China Architecture & Building Press, CN (3 pages).

Lian, Peisheng, "Atomic Energy Industry," May 2002, p. 330, ISBN 7-5022-2453-X, Atomic Energy Press, CN (3 pages).

Office Action (Notice of Reasons for Rejection) issued on May 23, 2023, by the Japanese Patent Office in corresponding Japanese Patent Application No. 2020-567036, and an English Translation of the Office Action. (14 pages).

Examination Report Under Sections 12 & 13 of the Patents Act, mailed Apr. 27, 2022 in IN Application No. 202017051057, Intellectual Property India, New Delhi, IN, 6 pages.

Marcus, "The Effectivity of Solvents as Electron Pair Donors", Journal of Solution Chemistry, vol. 13, No. 9, 1984 (month unknown), pp. 599-624.

U.S. Appl. No. 17/057,302, Leduc et al.

U.S. Appl. No. 17/058,725, Leduc et al.

U.S. Appl. No. 17/058,730, Leduc et al.

International Search Report (PCT/ISA/210) and Written Opinion (PCT/ISA/237), with English-language translation, mailed Aug. 6, 2019 in PCT/FR2019/051238, 27 pages, European Patent Office, Rijswijk, NL.

Coutellerie-Ap., "Les Principaux Aciers Utilises en Coutellerie", Jan. 1, 2016, pp. 1-3, Retrieved from the Internet Dec. 12, 2018: http://www.coutellerie-ap.fr/liste/ (XP055533233).

Wikipedia, "Acier inoxydable", Oct. 15, 2004, pp. 1-11, Retrieved from the Internet Dec. 12, 2018: https://fr.wikipedia.org/wiki/Acier_inoxydable (XP055533223).

Wikipedia, "Hastelloy", Mar. 2, 2009, pp. 1-2, Retrieved from the Internet Dec. 12, 2018: https://fr.wikipedia.org/wiki/Hastelloy (XP055533203).

Wikipedia, "Inconel", Mar. 28, 2009, pp. 1-3, Retrieved from the Internet Dec. 12, 2018: https://fr.wikipedia.org/wiki/Inconel (XP055533228).

International Search Report (PCT/ISA/210) and Written Opinion (PCT/ISA/237), with English-language translation, mailed Jan. 24, 2020 in PCT/FR2019/051239, 31 pages, European Patent Office, Rijswijk, NL.

International Search Report (with English Translation) and Written Opinion, with English-language translations, mailed Oct. 9, 2019 in PCT/FR2019/051250, 21 pages, European Patent Office, Rijswijk, NL.

(56) References Cited

OTHER PUBLICATIONS

**Leduc, Philippe, et al., U.S. Appl. No. 17/057,302 entitled Method for Producing a Lithium Bis(fluorosulfonyl)imide Salt, filed in the U.S. Patent and Trademark Office Nov. 20, 2020.
**Leduc, Philippe, et al., U.S. Appl. No. 17/058,725 entitled Method for Producing a Lithium Bis(fluorosulfonyl)imide Salt, filed in the U.S. Patent and Trademark Office Nov. 25, 2020.
**Leduc, Philippe, et al., U.S. Appl. No. 17/058,730 entitled Process for Purifying a Lithium Bis(fluorosulfonyl)imide Salt, filed in the U.S. Patent and Trademark Office Nov. 25, 2020.
Office Action (Decisionof Refusal) issued on Dec. 26, 2023, by the Japanese Patent Office in corresponding Japanese Patent Application No. 2020-566239, and an English Translation of the Office Action. (15 pages).
Office Action (Request for the Submission of on Opinion) issued on Jan. 17, 2024, by the Intellectual Property Office in corresponding Korean Patent Application No. 10-2020-7033827, and an English Translation of the Office Action. (10 pages).
Office Action (Third Party Observation) issued on Jan. 15, 2024, by the European Patent Office in corresponding European Application No. 20190737832, 4 pages.
Davis, J."Stainless steel reference #1" Wikipedia (Retrieved Jan. 23, 2024), edited by Joseph Davis (1994)., 25 Pages.
Office Action issued by the U.S. Patent and Trademark Office in the U.S. Appl. No. 17/058,725, mailed on Jan. 29, 2024, U.S. Patent and Trademark Office, Alexandria, VA. (26 pages).
Office Action issued by the U.S. Patent and Trademark Office in the U.S. Appl. No. 17/059,856 mailed on Jan. 9, 2024, U.S. Patent and Trademark Office, Alexandria, VA. (21 pages).
Office Action (Decision of Refusal) issued on May 16, 2023, by the Japanese Patent Office in corresponding Japanese Patent Application No. 2020-567031, and an English Translation of the Office Action. (6 pages).
A Notice of Filing of a Third Party Observation issued on Aug. 21, 2024 by the Intellectual Property Office in Korean Patent Application No. 10-2020-7033827, 2 pages, English Translation only.
Office Action (Request for the Submission of an Opinion) issued on Aug. 21, 2024, by the Intellectual Property Office in Korean Patent Application No. 10-2020-7034213, and an English Translation of the Office Action. (11 pages).
"Autoclave", Wikipedia, downloaded Jun. 27, 2024.
Office Action issued by the U.S. Patent and Trademark Office in the U.S. Appl. No. 17/058,725, mailed Jul. 5, 2024 U.S. Patent and Trademark Office, Alexandria, VA. (11 pages).

* cited by examiner

METHOD FOR PREPARING IMIDE SALTS CONTAINING A FLUOROSULFONYL GROUP

FIELD OF THE INVENTION

The present invention relates to a process for preparing imide salts containing a fluorosulfonyl group.

TECHNICAL BACKGROUND

By virtue of their very low basicity, anions of sulfonylimide type are increasingly used in the field of energy storage in the form of inorganic salts in batteries, or of organic salts in supercapacitors or in the field of ionic liquids. Since the battery market is in full expansion and reduction of battery manufacturing costs has become a major challenge, an inexpensive large-scale process for synthesizing anions of this type is necessary.

In the specific field of Li-ion batteries, the salt that is currently the most widely used is $LiPF_6$, but this salt has many drawbacks such as limited thermal stability, sensitivity to hydrolysis and thus lower safety of the battery. Recently, novel salts bearing the group $FSO_2$— have been studied and have demonstrated many advantages such as better ion conductivity and resistance to hydrolysis. One of these salts, LiFSI ($LiN(FSO_2)_2$), has shown highly advantageous properties which make it a good candidate for replacing $LiPF_6$.

The majority of the processes for preparing imide salts containing a fluorosulfonyl group comprise numerous steps, the consequence of which is the formation of byproducts which have physical properties such that their removal may prove to be complex and/or may necessitate expensive purification steps. Moreover, the accumulation of steps may give rise to a reduction in the final yields of LiFSI. Furthermore, certain processes cannot be applied on an industrial scale and/or give rise to effluents that may be difficult to process. As a function of the complexity required for the purification steps, the amount of effluents generated may be very large and may thus entail substantial processing costs.

There is thus a need for a process for preparing imide salts containing a fluorosulfonyl group which does not have at least one of the abovementioned drawbacks.

DESCRIPTION OF THE INVENTION

The present invention relates to a process for preparing a compound of formula (III) below:

$$R_2\text{—}(SO_2)\text{—}NM\text{—}(SO_2)\text{—}F \quad \text{(III)}$$

in which:

$R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_2$ preferably representing F;

M represents a monovalent or divalent cation; M preferably represents a monovalent cation;

said process comprising:

a step b) of fluorination of a compound of formula (I) below:

$$R_1\text{—}(SO_2)\text{—}NH\text{—}(SO_2)\text{—}Cl \quad \text{(I)}$$

in which $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_1$ preferably representing Cl;

with at least one fluorinating agent, preferably in the presence of at least one organic solvent OS1;

a step c) of distillation of the composition obtained in step b), said composition comprising a compound of formula (II) below:

$$R_2\text{—}(SO_2)\text{—}NH\text{—}(SO_2)\text{—}F \quad \text{(II)}.$$

The process according to the invention may comprise an optional step d) of dissolving the composition obtained in step c) in an organic solvent OS2.

According to one embodiment, the process according to the invention comprises a step e) of placing the composition obtained in step c) or in step d) in contact with a composition comprising at least one alkali metal or alkaline-earth metal salt, to give a compound of formula (III) below:

$$R_2\text{—}(SO_2)\text{—}NM\text{—}(SO_2)\text{—}F \quad \text{(III)}$$

$R_2$ and M being as defined above.

The process according to the invention may comprise a cation-exchange step f) to convert a compound of formula (III) into another compound of formula (III), but for which M is different.

Preferably, the present invention relates to a process for preparing a compound of formula (III) as defined previously, said process comprising:

a step a) of reacting a sulfamide of formula (A) below:

$$R_0\text{—}(SO_2)\text{—}NH_2 \quad \text{(A)}$$

in which $R_0$ represents one of the following radicals: OH, Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_0$ preferably representing OH;

with at least one sulfur-based acid and at least one chlorinating agent, to form a compound of formula (I):

$$R_1\text{—}(SO_2)\text{—}NH\text{—}(SO_2)\text{—}Cl \quad \text{(I)}$$

in which $R_1$ represents one of the following radicals: Cl, F, $CF_3$, CH $F_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{16}$, $C_8F_{17}$ or $C_9F_{19}$, $R_1$ preferably representing Cl;

a step b) of fluorination of a compound of formula (I) as defined above with at least one fluorinating agent, preferably in the presence of at least one organic solvent OS1;

a step c) of distillation of the composition obtained in step b), said composition comprising a compound of formula (II) below:

$$R_2\text{—}(SO_2)\text{—}NH\text{—}(SO_2)\text{—}F \quad \text{(II)}.$$

The process according to the invention advantageously solves at least one of the drawbacks of the existing processes. It advantageously enables:

the preparation of a compound of formula (III), for instance LiFSI, on an industrial scale, and at reduced cost; and/or the preparation of a compound of formula (III), for instance LiFSI, of high purity, which notably allows it to be used in the electrolytes of Li-ion batteries; and/or reduction of the effluents to be processed.

Chlorination Step a)

According to one embodiment, the abovementioned process also comprises a step a), prior to step b), comprising the reaction of a sulfamide of formula (A) below:

$$R_0\text{—}(SO_2)\text{—}NH_2 \quad \text{(A)}$$

in which $R_0$ represents one of the following radicals: OH, Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;

with at least one sulfur-based acid and at least one chlorinating agent, to form a compound of formula (I) as defined above.

Preferably, compound (A) is that in which $R_0$ represents OH.

Step a) may be performed:

at a temperature of between 30° C. and 150° C., and/or with a reaction time of between 1 hour and 7 days; and/or at a pressure of between 1 bar abs and 20 bar abs.

According to the invention, the sulfur-based agent may be chosen from the group consisting of chlorosulfonic acid ($ClSO_3H$), sulfuric acid, oleum and mixtures thereof.

According to the invention, the chlorinating agent may be chosen from the group consisting of thionyl chloride ($SOCl_2$), oxalyl chloride $(COCl)_2$, phosphorus pentachloride ($PCl_5$), phosphonyl trichloride ($PCl_3$), phosphoryl trichloride ($POCl_3$) and mixtures thereof.

Preferably, the chlorinating agent is thionyl chloride.

The chlorination step a) may be performed in the presence of a catalyst chosen, for instance, from a tertiary amine (such as methylamine, triethylamine or diethylmethylamine); pyridine; and 2,6-lutidine. The mole ratio between the sulfur-based acid and compound (A) (in particular in which $R_0$=OH) may be between 0.7 and 5, preferably between 0.9 and 5.

The mole ratio between the chlorinating agent and compound (A) (in particular in which $R_0$=OH) may be between 2 and 10, preferably between 2 and 5.

In particular, when the sulfur-based agent is chlorosulfonic acid, the mole ratio between the latter and compound (A) (in particular in which $R_0$=OH) is between 0.9 and 5, and/or the mole ratio between the chlorinating agent and compound (A), in particular with $R_0$=OH, is between 2 and 5.

In particular, when the sulfur-based agent is sulfuric acid (or oleum), the mole ratio between the sulfuric acid (or oleum) and compound (A) (in particular in which $R_0$=OH), is between 0.7 and 5.

In particular, when the sulfur-based agent is sulfuric acid (or oleum), the mole ratio between the sulfuric acid (or oleum) and compound (A) (in particular in which $R_0$=OH) is between 0.9 and 5, and/or the mole ratio between the chlorinating agent and compound (A) (in particular in which $R_0$=OH) is between 2 and 10.

Step a) advantageously allows the formation of a compound of formula (I):

$$R_1—(SO_2)—NH—(SO_2)—Cl \quad (I)$$

in which $R_1$ is as defined previously, and in particular in which $R_1$ represents Cl.

Fluorination Step b)

The process according to the invention comprises a step b) of fluorination of a compound of formula (I) below:

$$R_1—(SO_2)—NH—(SO_2)—Cl \quad (I)$$

in which $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_1$ preferably representing Cl;

with at least one fluorinating agent, preferably in the presence of at least one organic solvent OS1.

Step b) notably allows the fluorination of the compound of formula (I) to a compound of formula (II):

$$R_2—(SO_2)—NH—(SO_2)—F \quad (II)$$

in which $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_2$ preferably representing F.

Preferably, in formula (II) above, $R_2$ represents F, $CF_3$, $CHF_2$ or $CH_2F$. Particularly preferably, $R_2$ represents F.

According to one embodiment, the fluorinating agent is chosen from the group consisting of HF (preferably anhydrous HF), KF, $AsF_3$, $BiF_3$, $ZnF_2$, $SnF_2$, $PbF_2$, $CuF_2$, and mixtures thereof, the fluorinating agent preferably being HF, and even more preferentially anhydrous HF. In the context of the invention, the term “anhydrous HF” means HF containing less than 500 ppm of water, preferably less than 300 ppm of water, preferably less than 200 ppm of water.

Step b) of the process is preferably performed in at least one organic solvent OS1. The organic solvent OS1 preferably has a donor number of between 1 and 70 and advantageously between 5 and 65. The donor number of a solvent represents the value −ΔH, ΔH being the enthalpy of the interaction between the solvent and antimony pentachloride (according to the method described in *Journal of Solution Chemistry*, vol. 13, No. 9, 1984). As organic solvent OS1, mention may notably be made of esters, nitriles, dinitriles, ethers, diethers, amines, phosphines, and mixtures thereof.

Preferably, the organic solvent OS1 is chosen from the group consisting of methyl acetate, ethyl acetate, butyl acetate, acetonitrile, propionitrile, isobutyronitrile, glutaronitrile, dioxane, tetrahydrofuran, triethylamine, tripropylamine, diethylisopropylamine, pyridine, trimethylphosphine, triethylphosphine, diethylisopropylphosphine, and mixtures thereof. In particular, the organic solvent OS1 is dioxane.

Step b) may be performed at a temperature of between 0° C. and the boiling point of the organic solvent OS1 (or of the organic solvent mixture OS1). Preferably, step b) is performed at a temperature of between 5° C. and the boiling point of the organic solvent OS1 (or of the organic solvent mixture OS1), preferentially between 20° C. and the boiling point of the organic solvent OS1 (or of the organic solvent mixture OS1).

Step b), preferably with anhydrous hydrofluoric acid, may be performed at a pressure P, preferably between 0 and 16 bar abs.

This step b) is preferably performed by dissolving the compound of formula (I) in the organic solvent OS1, or the mixture of organic solvents OS1, prior to the step of reaction with the fluorinating agent, preferably with anhydrous HF.

The mass ratio between the compound of formula (I) and the organic solvent OS1, or the mixture of organic solvents OS1, is preferably between 0.001 and 10, and advantageously between 0.005 and 5.

According to one embodiment, anhydrous HF is introduced into the reaction medium, preferably in gaseous form.

The mole ratio x between the fluorinating agent, preferably anhydrous HF, and the compound of formula (I) used is preferably between 1 and 10, and advantageously between 1 and 5.

The step of reacting with the fluorinating agent, preferably anhydrous HF, may be performed in a closed medium or in an open medium; preferably, step b) is performed in an open medium notably with evolution of HCl in gas form.

The fluorination reaction typically leads to the formation of HCl, the majority of which may be degassed from the reaction medium (just like the excess HF if the fluorinating agent is HF), for example by stripping with a neutral gas (such as nitrogen, helium or argon).

However, the residual HF and/or HCl may be dissolved in the reaction medium. In the case of HCl, the amounts are very low since, at the working pressures and temperature, HCl is mainly in gas form.

The composition obtained on conclusion of step b) may be stored in an HF-resistant container.

The composition obtained in step b) may comprise HF (it is in particular unreacted HF), the compound of the above-mentioned formula (II), the solvent OS1 (for instance dioxane), and optionally HCl, and/or optionally heavy compounds.

Distillation Step c)

The process according to the invention comprises a step c) of distillation of the composition obtained in step b), said composition comprising a compound of formula (II) below:

$$R_2\text{—}(SO_2)\text{—}NH\text{—}(SO_2)\text{—}F \qquad (II).$$

According to one embodiment, step c) of distillation of the composition obtained in step b) makes it possible to form and to recover:

- a first stream F1 comprising HF, optionally the organic solvent OS1 and/or optionally HCl, preferably at the top of the distillation column, said stream F1 being gaseous or liquid;
- a second stream F2 comprising the compound of formula (II), and optionally heavy compounds, preferably at the bottom of the distillation column, said stream F2 preferably being liquid.

When stream F2 comprises heavy compounds, it may be subjected to an additional distillation step in a second distillation column, to form and to recover:

- a stream F2-1 comprising the compound of formula (II), free of heavy compounds, preferably at the top of the distillation column, said stream F2-1 preferably being liquid,
- a stream F2-2 comprising the heavy compounds and the compound of formula (II), preferably at the bottom of the distillation column, said stream F2-2 containing less than 10% by weight of the compound of formula (II) contained in the composition obtained in step b), preferably less than 7% by weight and preferentially less than 5% by weight, said stream F2-2 preferably being liquid.

According to one embodiment, step c) of distillation of the composition obtained in step b) makes it possible to form and to recover, by means of using two distillation columns:

- a first stream F1 comprising HF, optionally the organic solvent OS1 and/or optionally HCl, at the top of the first distillation column, said stream F1 being gaseous or liquid;
- a second stream F2 comprising the compound of formula (II), and optionally heavy compounds, at the bottom of the first distillation column, said stream F2 preferably being liquid;

said stream F2 being subjected to a distillation step in a second distillation column, to form and to recover:

- a stream F2-1 comprising the compound of formula (II), free of heavy compounds, at the top of the second distillation column, said stream F2-1 preferably being liquid,
- a stream F2-2 comprising the heavy compounds and the compound of formula (II), at the bottom of the second distillation column, said stream F2-2 containing less than 10% by weight of the compound of formula (II) contained in the composition obtained in step b), preferably less than 7% by weight and preferentially less than 5% by weight, said stream F2-2 preferably being liquid.

In the context of the invention, the term "heavy compounds" means organic compounds with a boiling point higher than that of the compound of formula (II). They may result from cleavage reactions of the compound of formula (I), leading, for example, to compounds such as $FSO_2NH_2$, and/or from solvent degradation reactions, leading to the formation of oligomers.

According to one embodiment, step c) of distillation of the composition obtained in step b) makes it possible to form and to recover:

- a first stream F'1 comprising HF, optionally the organic solvent OS1 and/or optionally HCl, preferably at the top of the distillation column, said stream F'1 being gaseous or liquid;
- a second stream F'2 comprising the compound of formula (II), preferably recovered by side removal, said stream F'2 preferably being liquid;
- a third stream F'3 comprising heavy compounds and the compound of formula (II), preferably at the bottom of the distillation column, said stream F'3 containing less than 10% by weight of the compound of formula (II) contained in the composition obtained in step b), preferably less than 7% by weight and preferentially less than 5% by weight, said stream F'3 preferably being liquid.

To perform the side removal, the distillation column may contain at least one tray.

The distillation step c) may be performed at a pressure ranging from 0 to 5 bar abs, preferably from 0 to 3 bar abs, preferentially from 0 to 2 bar abs and advantageously from 0 to 1 bar abs.

The distillation step c) may be performed:

- at a distillation column bottom temperature ranging from 150° C. to 200° C., preferably from 160° C. to 180° C. and preferentially from 165° C. to 175° C., at a pressure of 1 bar abs; or
- at a distillation column bottom temperature ranging from 30° C. to 100° C., preferably from 40° C. to 90° C. and preferentially from 40° C. to 85° C., at a pressure of 0.03 bar abs.

The distillation step c) may be performed in any conventional device. Such a device may be a distillation device comprising a distillation column, a boiler and a condenser.

The distillation column may comprise:

- at least one packing, for instance random packing and/or structured packing, and/or
- trays, for instance perforated trays, fixed valve trays, movable valve trays, bubble trays or combinations thereof.

The height of the distillation column typically depends on the nature of the compounds to be separated. Typically, depending on the flow rates used, the distillation column may have any type of diameter: small (less than or equal to 1 meter) or high (greater than 1 meter).

The material of the distillation column, of its internal constituents (packing and/or trays), of the boiler and/or of the condenser is advantageously chosen from corrosion-resistant materials, on account of the potential presence of HF and/or HCl in the composition subjected to distillation.

The corrosion-resistant materials may be chosen from enamelled steels, nickel, titanium, chromium, graphite, silicon carbides, nickel-based alloys, cobalt-based alloys, chromium-based alloys, steels partially or totally coated with a fluoropolymer protective coating (for instance PVDF: polyvinylidene fluoride, PTFE: polytetrafluoroethylene, PFA:

copolymer of $C_2F_4$ and of perfluorinated vinyl ether, FEP: copolymer of $C_2F_4$ and of $C_3F_6$, ETFE: copolymer of ethylene and of tetrafluoroethylene, or FKM: copolymer of hexafluoropropylene and of difluoroethylene).

The nickel-based alloys are preferably alloys comprising at least 40% by weight of nickel, preferably at least 50% by weight of nickel, relative to the total weight of the alloy. Examples that may be mentioned include the alloys Inconel®, Hastelloy® or Monel®.

The streams F1 and F'1 may comprise HF, HCl and the organic solvent OS1 (in particular dioxane).

According to one embodiment, stream F1 comprises from 2% to 70% by weight of HF, preferably from 5% to 60% by weight of HF, relative to the total weight of stream F1, and from 30% to 98% by weight of organic solvent OS1, preferably from 40% to 95% by weight of OS1, relative to the total weight of stream F1.

According to one embodiment, stream F'1 comprises from 2% to 70% by weight of HF, preferably from 5% to 60% by weight of HF, relative to the total weight of stream F'1, and from 30% to 98% by weight of organic solvent OS1, preferably from 40% to 95% by weight of OS1, relative to the total weight of stream F'1.

According to one embodiment, stream F2 comprises from 50% to 100% by weight of compound of formula (II), preferably from 70% to 99% by weight of compound of formula (II), relative to the total weight of stream F2.

According to one embodiment, stream F'2 comprises from 50% to 100% by weight of compound of formula (II), preferably from 70% to 99% by weight of compound of formula (II), relative to the total weight of stream F'2.

According to one embodiment, stream F2-1 comprises from 50% to 100% by weight of compound of formula (II), preferably from 70% to 99% by weight of compound of formula (II), relative to the total weight of stream F2-1.

Step c) advantageously allows the recovery of a high-purity compound of formula (II). The use of a high-purity compound of formula (II) advantageously makes it possible to prepare a high-purity compound of formula (III), notably LiFSI, without the need for additional purification steps.

Step d)

According to one embodiment, the process according to the invention comprises a step d) of dissolving the composition obtained in step c) in an organic solvent OS2, said solvent OS2 preferably being a polar aprotic solvent.

The organic solvent OS2 may be a water-miscible solvent.

In the context of the invention, the term “water-miscible solvent” means a solvent not forming a macroscopic phase separation.

The organic solvent OS2 may be chosen from the group consisting of ethers, diethers, nitriles, amines, carbonates and phosphines. Preferably, the organic solvent OS2 is chosen from the group consisting of methyl acetate, ethyl acetate, butyl acetate, acetonitrile, propionitrile, isobutyronitrile, glutaronitrile, dioxane, tetrahydrofuran, triethylamine, tripropylamine, diethylisopropylamine, pyridine, diethyl carbonate, dimethyl carbonate, ethyl methyl carbonate, ethylene carbonate, trimethylphosphine, triethylphosphine, diethylisopropylphosphine, and mixtures thereof, the solvent OS2 preferentially being dioxane or butyl acetate or acetonitrile, and advantageously dioxane.

Preferably, step d) comprises the addition of said solvent OS2 to the composition obtained in step b) or in step c).

In the embodiment in which the process comprises step c), step d) notably comprises the dissolution of stream F2 (or of stream F2-1 or of stream F'2) in an organic solvent OS2.

Step e)

According to one embodiment, the process according to the invention comprises a step e) of placing the composition obtained in step c) or in step d) in contact with a composition comprising at least one alkali metal or alkaline-earth metal salt, to give a compound of formula (III) below:

$$R_2\text{—}(SO_2)\text{—}NM\text{—}(SO_2)\text{—}F$$

$R_2$ and M being as defined above.

Step e) advantageously allows the compound of formula (II) to be converted into an abovementioned compound of formula (III):

$$R_2\text{—}(SO_2)\text{—}NM\text{—}(SO_2)\text{—}F \qquad \text{(III)}$$

in which:

- $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_2$ preferably representing F; and
- M represents a monovalent cation, preferably $K^+$ or $Li^+$ or $Na^+$, or a divalent cation, M preferably representing a monovalent cation.

Typically, step e) may be performed using the composition obtained in step c) (stream F2, or stream F2-1 or stream F'2), or using the composition obtained in step d) or after any intermediate step between step c) and step e).

According to one embodiment, the composition comprising at least one alkali metal or alkaline-earth metal salt is an aqueous composition, preferably an aqueous suspension or an aqueous solution.

According to another embodiment, the composition comprising at least one alkali metal or alkaline-earth metal salt is a solid composition; preferably, the composition consists of at least one alkali metal or alkaline-earth metal salt.

The step of placing in contact may correspond to the addition of the composition obtained in step c) or step d) to the composition comprising at least one alkali metal or alkaline-earth metal salt, or vice versa. Preferably, the composition obtained in step c) or d) is added to the composition comprising at least one alkali metal or alkaline-earth metal salt.

Step e) may be performed in a reactor, preferably comprising at least one stirring system.

The alkali metal or alkaline-earth metal salt may be a salt of the cation M.

According to one embodiment, the alkali metal or alkaline-earth metal salt is chosen from the group consisting of MOH, $MOH.H_2O$, $MHCO_3$, $M_2CO_3$, MCl, $M(OH)_2$, $M(OH)_2.H_2O$, $M(HCO_3)_2$, $MCO_3$, $MCl_2$, and mixtures thereof, M being as defined previously. Preferably, the alkali metal or alkaline-earth metal salt is chosen from the group consisting of MOH, $MOH.H_2O$, $MHCO_3$, $M_2CO_3$, MCl, and mixtures thereof.

Preferably, the alkali metal or alkaline-earth metal salt is chosen from the group consisting of LiOH, $LiOH.H_2O$, $LiHCO_3$, $Li_2CO_3$, LiCl, KOH, KOH $H_2O$, $KHCO_3$, $K_2CO_3$, KCl, NaOH, $NaOH.H_2O$, $NaHCO_3$, $Na_2CO_3$, NaCl, and mixtures thereof, the salt preferably being a potassium salt, and advantageously $K_2CO_3$.

When it is an aqueous composition comprising at least one alkali metal or alkaline-earth metal salt, the composition may be prepared by any conventional means for preparing an alkaline aqueous composition. Such a means may be, for example, dissolution of the alkali metal or alkaline-earth metal salt in ultrapure or deionized water, with stirring.

Preferably, the abovementioned process comprises a step e) comprising the addition of the composition obtained in step c) or step d), said composition comprising a compound of the abovementioned formula (II):

$$R_2\text{—}(SO_2)\text{—}NH\text{—}(SO_2)\text{—}F \quad (II),$$

$R_2$ being as defined previously, and $R_2$ preferably representing F, in an aqueous composition comprising at least one potassium salt or one lithium salt, preferably a potassium salt.

To determine the amount of alkali metal or alkaline-earth metal salt to be introduced, it is typically possible to perform an analysis of the total acidity of the mixture to be neutralized.

According to one embodiment, step e) is such that:

the mole ratio of the alkali metal or alkaline-earth metal salt divided by the number of basicities of said salt relative to the compound of formula (II) is greater than or equal to 1, preferably less than 5, preferably less than 3, preferentially between 1 and 2; and or the mass ratio of the alkali metal or alkaline-earth metal salt to the mass of water in the aqueous composition is between 0.1 and 2, preferably between 0.2 and 1, preferably between 0.3 and 0.7.

For example, the salts $Li_2CO_3$ and $K_2CO_3$ each have a number of basicities equal to 2.

Step e) of the process according to the invention may be performed at a temperature of less than or equal to 40° C., preferably less than or equal to 30° C., preferentially less than or equal to 20° C., and in particular less than or equal to 15° C.

According to one embodiment, the the process according to the invention comprises an additional step of filtering the composition obtained in step e), resulting in a filtrate F and a cake G.

The compound of formula (III) prepared may be contained in the filtrate F and/or in the cake G.

The filtrate F may be subjected to at least one extraction step with an organic solvent OS3 which is typically sparingly soluble in water, in order to extract the abovementioned compound of formula (III) into an organic phase. The extraction step typically results in the separation of an aqueous phase and an organic phase.

In the context of the invention, and unless otherwise mentioned, the term "sparingly soluble in water" refers to a solvent whose solubility in water is less than 5% by weight.

The abovementioned organic solvent OS3 is in particular chosen from the following families: esters, nitriles, ethers, chlorinated solvents and aromatic solvents, and mixtures thereof. Preferably, the organic solvent OS3 is chosen from dichloromethane, ethyl acetate, butyl acetate, tetrahydrofuran and diethyl ether, and mixtures thereof. In particular, the organic solvent OS3 is butyl acetate.

For each extraction, the mass amount of organic solvent used may range between ⅙ and 1 times the mass of the filtrate F. The number of extractions may be between 2 and 10.

Preferably, the organic phase, resulting from the extraction(s), has a mass content of compound of formula (III) ranging from 5% to 40% by mass.

The separated organic phase (obtained on conclusion of the extraction) may then be concentrated to reach a concentration of compound of formula (III) of between 30% and 60%, preferably between 40% and 50% by mass, said concentration possibly being achieved by any evaporation means known to those skilled in the art.

The abovementioned cake G may be washed with an organic solvent OS4 chosen from the following families: esters, nitriles, ethers, chlorinated solvents and aromatic solvents, and mixtures thereof. Preferably, the organic solvent OS4 is chosen from dichloromethane, ethyl acetate, butyl acetate, tetrahydrofuran, acetonitrile and diethyl ether, and mixtures thereof. In particular, the organic solvent OS4 is butyl acetate.

The mass amount of organic solvent OS4 used may range between 1 and 10 times the weight of the cake. The total amount of organic solvent OS4 intended for the washing may be used in a single portion or in several portions for the purpose notably of optimizing the dissolution of the compound of formula (III).

Preferably, the organic phase, resulting from the washing of the cake G, has a mass content of compound of formula (III) ranging from 5% to 20% by mass.

The separated organic phase resulting from the washing of the cake G may then be concentrated to reach a concentration of compound of formula (III) of between 30% and 60%, preferably between 40% and 50% by mass, said concentrating operation possibly being achieved by any evaporation means known to those skilled in the art.

According to one embodiment, the organic phases resulting from the extraction of the filtrate F and from the washing of the cake G may be pooled, before the concentration step.

Cation-Exchange Step f)

The process according to the invention may comprise, after step e), a cation-exchange step f) to convert a compound of formula (III) into another compound of formula (III), but for which M represents a different monovalent cation.

Preferably, this step comprises the reaction between a compound of formula (III) obtained in the preceding step e):

$$R_2\text{—}(SO_2)\text{—}NM\text{—}(SO_2)\text{—}F \quad (III)$$

in which:

$R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_2$ preferably representing F;

M represents a monovalent or divalent cation, preferably a monovalent cation;

with an alkali metal or alkaline-earth metal salt, the cation of which is other than M (for example M').

For example, if the compound of formula (III) obtained in step e) is a compound for which M represents $K^+$, then the process may comprise a step f) of cation exchange of this compound with an alkali metal or alkaline-earth metal salt, the cation of which is not $K^+$, for example with a lithium salt.

For example, if step e) leads to a compound of formula (III-A):

$$R_2\text{—}(SO_2)\text{—}NM\text{—}(SO_2)\text{—}F \quad (III\text{-}A)$$

in which:

$R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_6F_{11}$, $C_6F_{13}$, $C_7F_{15}$, $C_8F_{17}$ or $C_9F_{19}$, $R_2$ preferably representing F;

M represents a monovalent or divalent cation, preferably a monovalent cation;

the process may comprise a step f) of cation exchange of the compound of formula (III-A) to a compound of formula (III-B):

$$R_2\text{—}(SO_2)\text{—}NM'\text{—}(SO_2)\text{—}F \quad (III\text{-}B)$$

in which:

$R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_2$ preferably representing F;

M' represents a monovalent cation other than M.

Purification Step q)

The process according to the invention may also comprise a step of purifying the compound of the abovementioned formula (III).

This step may be performed on conclusion of step e) or on conclusion of step f).

Step g) of purifying the compound of formula (III) may be performed by any known conventional method. It may be, for example, an extraction method, a solvent-washing method, a reprecipitation method, a recrystallization method, or a combination thereof.

On conclusion of the abovementioned step e) or of the abovementioned step f), the compound of formula (III) may be in the form of a composition comprising from 30% to 95% by weight of compound of formula (III) relative to the total weight of said composition.

According to a first embodiment, step g) is a step of crystallizing the abovementioned compound of formula (III).

Preferably, during step g), the abovementioned compound of formula (III) is crystallized under cold conditions, notably at a temperature of less than or equal to 25° C.

Preferably, during step g), the crystallization of the compound of formula (III) is performed in an organic solvent OS5 (crystallization solvent) chosen from chlorinated solvents, for instance dichloromethane, and aromatic solvents, for instance toluene, in particular at a temperature of less than or equal to 25° C. Preferably, the compound of formula (III) crystallized on conclusion of step d) is recovered by filtration.

The crystallization step is preferably performed on a composition comprising between 75% and 90% by weight of the compound of formula (III). To do this, the composition obtained on conclusion of step e) or f) may be concentrated to obtain a solution corresponding to the abovementioned composition. The concentrating operation may be performed by any conventional concentration means. It may notably be performed under a reduced pressure of between 40 mbar and 0.01 mbar at a temperature below 70° C., preferentially below 50° C., preferably below 40° C. It may preferably be performed under the conditions of step v) described below.

According to a second embodiment, step g) comprises the following steps:

i) optional dissolution of the compound of formula (III) in an organic solvent S'1;
ii) addition of deionized water to dissolve and extract the compound of the abovementioned formula (III), forming an aqueous solution of said compound of formula (III);
iii) optional concentration of said aqueous solution of said compound of formula (III);
iv) extraction of the compound of formula (III) from said aqueous solution, with an organic solvent S'2, said solvent S2 preferably forming an azeotropic mixture with water, this step being repeated at least once;
v) concentration of the compound of formula (III) by evaporation of said organic solvent S'2 and of the water, in a short-path thin-film evaporator, under the following conditions:
   temperature of between 30° C. and 95° C., preferably between 30° C. and 90° C., preferentially between 40° C. and 85° C.;
   pressure of between $10^{-3}$ mbar abs and 5 mbar abs;
   residence time of less than or equal to 15 min, preferably less than or equal to 10 min and advantageously less than or equal to 5 min;
vi) optional crystallization of the compound of formula (III).

It is possible for step g) not to include the abovementioned step i), if the compound of formula (III) obtained in step e) or in step f) already comprises an organic solvent (for instance OS3 and/or OS4).

The abovementioned step ii) notably comprises the addition of deionized water to the solution of the compound of formula (III) to the abovementioned organic solvent S'1, to allow the dissolution of said compound of formula (III), and the extraction of said compound of formula (III) in water (aqueous phase).

The extraction may be performed via any known extraction means. The extraction typically allows the separation of an aqueous phase (aqueous solution of said salt in the present case) and of an organic phase.

According to the invention, step ii) may be repeated at least once, for example three times. In a first extraction, an amount of deionized water corresponding to half of the mass of the initial solution may be added, followed by an amount equal to about a third of the mass of the initial solution during the second extraction, and then an amount equal to about a quarter of the mass of the initial solution during the third extraction.

Preferably, step ii) is such that the mass of deionized water is greater than or equal to a third, preferably greater than or equal to half, of the mass of the initial solution of the compound of formula (III) in the organic solvent S'1 (in the case of a single extraction, or for the first extraction only if step ii) is repeated at least once).

In the case of multiple extractions (repetition of step ii)), the extracted aqueous phases may be pooled to form a single aqueous solution.

On conclusion of step ii), an aqueous solution of the compound of formula (III) is in particular obtained.

According to one embodiment, the mass content of compound of formula (III) in the aqueous solution is between 5% and 35%, preferably between 10% and 25%, relative to the total mass of the solution.

Preferably, step g) comprises a concentration step iii) between step ii) and step iv), preferably in order to obtain an aqueous solution of the compound of formula (III) comprising a mass content of compound of formula (III) of between 20% and 80%, in particular between 25% and 80%, preferably between 25% and 70% and advantageously between 30% and 65% relative to the total mass of the solution. The concentration step may be performed with a rotary evaporator under reduced pressure, at a pressure below 50 mbar abs (preferably below 30 mbar abs), and in particular at a temperature of between 25° C. and 60° C., preferably between 25° C. and 50° C., preferentially between 25° C. and 40° C., for example at 40° C.

The compound of formula (III), contained in the aqueous solution obtained on conclusion of step ii), and of an optional concentration step iii) or of an optional other intermediate step, may then be recovered by extraction with an organic solvent S'2, said solvent S'2 preferably being able to form an azeotrope with water (step iv). Step iv) leads in particular, after extraction, to an organic phase, saturated with water, containing the compound of formula (III) (it is a solution of the compound of formula (III) in the organic solvent S'2, said solution being saturated with water).

The extraction typically allows the separation of an aqueous phase and of an organic phase (solution of the compound of formula (III) in the solvent S'2 in the present case).

Step iv) advantageously allows the production of an aqueous phase and an organic phase, which are separated.

Preferably, the organic solvent S'2 is chosen from the group consisting of esters, nitriles, ethers, carbonates, chlorinated solvents and aromatic solvents, and mixtures thereof.

Preferably, the solvent S'2 is chosen from ethers and esters, and mixtures thereof. For example, mention may be made of diethyl carbonate, methyl t-butyl ether, cyclopentyl methyl ether, ethyl acetate, propyl acetate, butyl acetate, dichloromethane, tetrahydrofuran, acetonitrile and diethyl ether, and mixtures thereof. Preferably, the solvent S'2 is chosen from methyl t-butyl ether, cyclopentyl methyl ether, ethyl acetate, propyl acetate and butyl acetate, and mixtures thereof. In particular, the organic solvent S'2 is butyl acetate.

The extraction step iv) is repeated at least once, preferably from one to ten times and in particular four times. The organic phases may then be combined into a single phase before step v). For each extraction, the mass amount of organic solvent S'2 used may range between ⅙ and 1 times the mass of the aqueous phase. Preferably, the organic solvent S'2/water mass ratio, during an extraction of step iv), ranges from 1/6 to 1/1, the number of extractions ranging in particular from 2 to 10.

Preferably, during the extraction step iv), the organic solvent S'2 is added to the aqueous solution resulting from step ii) (and from the optional step iii)).

Step g) according to the second embodiment may comprise a preconcentration step between step iv) and step v), preferably to obtain a solution of the compound of formula (III) in the organic solvent S'2 comprising a mass content of compound of formula (III) of between 20% and 60%, and preferably between 30% and 50% by mass relative to the total mass of the solution. The preconcentration step may be performed at a temperature ranging from 25° C. to 60° C., preferably from 25° C. to 45° C., optionally under reduced pressure, for example at a pressure less than 50 mbar abs, in particular at a pressure less than 30 mbar abs. The preconcentration step is preferably performed with a rotary evaporator under reduced pressure, notably at 40° C. and at a pressure less than 30 mbar abs.

According to the invention, the concentration step v) may be performed at a pressure of between $10^{-2}$ mbar abs and 5 mbar abs, preferably between $5\times10^{-2}$ mbar abs and 2 mbar abs, preferentially between $5\times10^{-1}$ and 2 mbar abs, even more preferentially between 0.1 and 1 mbar abs and in particular between 0.4 and 0.6 mbar abs. In particular, step v) is performed at 0.5 mbar abs or at 0.1 mbar.

According to one embodiment, step v) is performed at a temperature of between 30° C. and 95° C., preferably between 30° C. and 90° C., preferentially between 40° C. and 85° C., and in particular between 50° C. and 70° C.

According to one embodiment, step v) is performed with a residence time of less than or equal to 15 minutes, preferentially less than 10 minutes, preferably less than or equal to 5 minutes and advantageously less than or equal to 3 minutes.

In the context of the invention, and unless otherwise mentioned, the term "residence time" means the time which elapses between the entry of the solution of the compound of formula (III) (in particular obtained on conclusion of the abovementioned step iv)) into the evaporator and the exit of the first drop of the solution.

According to a preferred embodiment, the temperature of the condenser of the short-path thin-film evaporator is between −50° C. and 5° C., preferably between −35° C. and 5° C. In particular, the condenser temperature is −5° C.

The abovementioned thin-film short-path evaporators are also known under the name "wiped-film short-path" (WFSP). They are typically referred to as such since the vapors generated during the evaporation cover a short path (travel a short distance) before being condensed in the condenser.

Among the short-path thin-film evaporators, mention may notably be made of the evaporators sold by the companies Buss SMS Ganzler ex Luwa AG, UIC GmbH or VTA Process.

Typically, the short-path thin-film evaporators may comprise a condenser for the solvent vapors placed inside the machine itself (in particular at the center of the machine), unlike other types of thin-film evaporator (which are not short-path evaporators) in which the condenser is outside the machine.

In this type of machine, the formation of a thin film, of product to be distilled, on the hot inner wall of the evaporator may typically be ensured by continuous spreading over the evaporation surface with the aid of mechanical means specified below.

The evaporator may notably be equipped, at its center, with an axial rotor on which are mounted the mechanical means that allow the formation of the film on the wall. They may be rotors equipped with fixed vanes, lobed rotors with three or four vanes made of flexible or rigid materials, distributed over the entire height of the rotor, or rotors equipped with mobile vanes, paddles, brushes, doctor blades or guided scrapers. In this case, the rotor may be constituted by a succession of pivot-articulated paddles mounted on a shaft or axle by means of radial supports. Other rotors may be equipped with mobile rollers mounted on secondary axles and said rollers are held tight against the wall by centrifugation. The spin speed of the rotor, which depends on the size of the machine, may be readily determined by a person skilled in the art. The various spindles may be made of various materials: metallic, for example steel, steel alloy (stainless steel), aluminum, or polymeric, for example polytetrafluoroethylene PTFE, or glass materials (enamel); metallic materials coated with polymeric materials.

Process

The process according to the invention may comprise intermediate steps between the various abovementioned steps of the process.

According to one embodiment, steps a), b), c) and optionally d) and e) are sequential.

According to one embodiment, the process according to the invention comprises:

a step a) of reacting a sulfamide of formula (A) below:

$$R_0\text{—}(SO_2)\text{—}NH_2 \quad (A)$$

in which $R_0$ represents one of the following radicals: OH, Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H^2F_7$, $C_4H_4F_5$, $C_5F_{11}$, $C_6F_{13}$, $C_7F_{15}$, $C_8F_{17}$ or $C_9F_{19}$, $R_0$ preferably representing OH;

with at least one sulfur-based acid and at least one chlorinating agent, to form a compound of formula (I):

$$R_1\text{—}(SO_2)\text{—}NH\text{—}(SO_2)\text{—}Cl \quad (I)$$

in which $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$, $R_1$ preferably representing Cl;

a step b) of fluorination of a compound of formula (I) with anhydrous HF in the presence of at least one organic solvent OS1, a step c) of distillation of the composition obtained in step b) to form and to recover a first stream F1 comprising HF, the organic solvent OS1 and optionally HCl, preferably at the top of the distillation column, said stream being gaseous or liquid;

a second stream F2 comprising the compound of the abovementioned formula (II), and optionally heavy compounds, preferably at the bottom of the distillation column, said stream F2 preferably being liquid;

an optional step d) of dissolving the composition obtained in step b) and comprising a compound of formula (II) (stream F2) in an organic solvent OS2;

a step e) of placing the composition obtained in step c), comprising a compound of the abovementioned formula (II) (stream F2), in contact with a composition, preferably an aqueous composition, comprising at least one alkali metal or alkaline-earth metal salt, to obtain a compound of formula (III) as defined previously.

The process according to the present invention is particularly advantageous for manufacturing the following compounds of formula (III): $LiN(SO_2F)_2$, $LiNSO_2CF_3SO_2F$, $LiNSO_2C_2F_5SO_2F$, $LiNSO_2CF_2OCF_3SO_2F$, $LiNSO_2C_3HF_6SO_2F$, $LiNSO_2C_4F_9SO_2F$, $LiNSO_2C_5F_{11}SO_2F$, $LiNSO_2C_6F_{13}SO_2F$, $LiNSO_2C_7F_{15}SO_2F$, $LiNSO_2C_8F_{17}SO_2F$, $LiNSO_2C_9F_{19}SO_2F$, $NaN(SO_2F)_2$, $NaNSO_2CF_3SO_2F$, $NaNSO_2C_2F_5SO_2F$, $NaNSO_2CF_2OCF_3SO_2F$, $NaNSO_2C_3HF_6SO_2F$, $NaNSO_2C_4F_9SO_2F$, $NaNSO_2C_5F_{11}SO_2F$, $NaNSO_2C_6F_{13}SO_2F$, $NaNSO_2C_7F_{15}SO_2F$, $NaNSO_2C_8F_{17}SO_2F$, $NaNSO_2C_9F_{19}SO_2F$ $KN(SO_2F)_2$, $KNSO_2CF_3SO_2F$, $KNSO_2C_2F_5SO_2F$, $KNSO_2CF_2OCF_3SO_2F$, $KNSO_2C_3HF_6SO_2F$, $KNSO_2C_4F_9SO_2F$, $KNSO_2C_5F_{11}SO_2F$, $KNSO_2C_6F_{13}SO_2F$, $KNSO_2C_7F_{15}SO_2F$, $KNSO_2C_8F_{17}SO_2F$ and $KNSO_2C_9F_{19}SO_2F$.

Preferably, the process according to the invention is a process for preparing $LiN(SO_2)_2$ (LiFSI).

In the context of the invention, the terms "lithium salt of bis(fluorosulfonyl)imide", "lithium bis(sulfonyl)imide", "LiFSI", "$LiN(SO_2F)_2$", "lithium bis(sulfonyl)imide" and "lithium bis(fluorosulfonyl)imide" are used equivalently.

The process according to the invention advantageously leads to a compound of formula (III), and in particular to LiFSI, in high purity, in particular at least equal to 99.5% by weight, advantageously at least equal to 99.95% by weight. In the context of the invention, the term "ppm" means ppm on a weight basis.

Uses

The present invention also relates to the use of the compound obtained via the process according to the invention in Li-ion batteries, notably in Li-ion battery electrolytes.

In particular, such batteries are Li-ion batteries of mobile devices (for example cellphones, cameras, tablets or laptop computers), or electric vehicles, or for storing renewable energy (such as photovoltaic or wind energy).

In the context of the invention, the term "between x and y" or "ranging from x to y" means a range in which the limits x and y are included. For example, the temperature "between −20 and 80° C." notably includes the values −20° C. and 80° C.

All the embodiments described above may be combined with each other. In particular, each embodiment of any step of the process of the invention may be combined with another particular embodiment.

The examples that follow illustrate the invention without, however, limiting it.

EXAMPLE

Example 1: Preparation of Bis(Fluorosulfonyl)Imide (HFSI)

107 g of bis(chlorosulfonyl)imide (HClSI) are dissolved in 320 g of butyl acetate in a stirred autoclave lined with a PFA jacket, equipped with a gas introduction tube and connected to a bubbler for trapping the HCl co-produced. The mixture is stirred. 25 g of HF are introduced via the introduction tube (i.e. an HF/HClSI mole ratio equal to 2.5) over 1 hour 30 minutes. The reaction is slightly exothermic. The temperature of the reaction medium rises from 18° C. to 29° C. during the operation. At the end of the introduction, a stream of nitrogen is passed through to strip out the excess HF.

The mixture obtained is introduced into a reactor equipped with a vacuum distillation column connected to a cardice trap. The pressure is adjusted to 12 mbar. Heating is commenced. A first distillation fraction is obtained between room temperature and 36° C. (vapor temperature). A second fraction distils at between 48° C. and 57° C. The distillation is then stopped.

This second fraction consists of 99% pure bis(fluorosulfonyl)imide (HFSI) (NMR analysis) and represents 53 g, i.e. a yield of 58%.

The NMR analysis conditions of the fluoro species by $^{19}F$ NMR, H1, are as follows:

The NMR spectra and quantifications were performed on a Brüker AV 400 spectrometer, at t 376.47 MHz for $^{19}F$, on a 5 mm probe of $BBFO^+$ type.

Example 2: preparation of the lithium salt of bis(fluorosulfonyl)imide (LiFSI)

40 g of HFSI from Example 1 (0.22 mol) are placed in 60 g of butyl acetate. 9.2 g of solid $Li_2CO_3$ (0.12 mol) are placed in a stirred and thermostatically regulated reactor equipped with a temperature probe. The mixture is left to react for 4 hours while maintaining the neutralization temperature below 15° C.

At the end of the neutralization, the reaction medium is recovered and filtered to remove the excess lithium carbonate. The cake is washed with 100 ml of butyl acetate.

The LiFSI is recovered in solution, NMR analysis of which does not detect any cleavage products, and ion chromatography analysis of which does not detect any sulfate, potassium or sodium.

The invention claimed is:

1. A process for preparing a compound of formula (III) below:

$$R_2\text{—}(SO_2)\text{—}NM\text{—}(SO_2)\text{—}F \qquad \text{(III)}$$

in which:

R2 represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$ M represents a monovalent or divalent cation;

said process comprising:

a step b) of fluorination of a compound of formula (I) below:

$$R_1\text{—}(SO_2)\text{—}NH\text{—}(SO_2)\text{—}C \qquad \text{(I)}$$

in which $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_5F_{17}$ or $C_9F_{19}$;

with at least one fluorinating agent being HF, and optionally at least one organic solvent OS1, at at pressure ranging from 1.5 to 16 bar to form a composition comprising a compound of formula (II) below:

$$R_2\text{—}(SO_2)\text{—}NH\text{—}(SO_2)\text{—}F \qquad \text{(II).}$$

in which $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_5F_{17}$ or $C_9F_{19}$;

a step c) of distilling the composition comprising the compound of formula (II) by means of using a single distillation column to form:

a recoverable first stream F'1 comprising HF, optionally the organic solvent OS1 and/or optionally HCI, said stream F'1 being gaseous or liquid recovered at the top of the distillation column, a recoverable second steam F'2 comprising the compound of formula (II), said stream F'2 recovered by a side removal of the distillation column; and a recoverable third stream F'3 comprising heavy compounds and the compound of formula (II), said stream F'3 containing less than 10% by weight of the compound of formula (II) contained in the composition obtained in step b), said stream F'3 recovered at the bottom of the distillation column; and a step e) of placing the stream F'2 comprising the compound of formula (II) in contact with a composition comprising at least one alkali metal or alkaline-earth metal salt, to give a compound of formula (III).

2. The process as claimed in claim 1, also comprising a step a), prior to step b), comprising the reaction of a sulfamide of formula (A) below:

$$R_0\text{—}(SO_2)\text{—}NH_2 \qquad \text{(A)}$$

in which $R_0$ represents one of the following radicals: OH, Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;

with at least one sulfur-based acid and at least one chlorinating agent, to form a compound of formula (I).

3. The process as claimed in claim 1, comprising a step d) of dissolving the composition obtained in step b) or the stream F'2 obtained in step c) in an organic solvent OS2.

4. The process as claimed in claim 3, wherein steps are performed, in sequence:

step b, step d), step c), and step e); or step b), step c), step d), and step e).

5. The process as claimed in claim 4, comprising a cation-exchange step f) to convert a compound of formula (III) into another compound of formula (III), but for which M is different.

6. The process as claimed in claim 4, in which:

the composition comprising at least one alkali metal or alkaline-earth metal salt is an aqueous composition; or the composition comprising at least one alkali metal or alkaline-earth metal salt is a solid composition.

7. The process as claimed in claim 1, in which the distillation step c) is performed at a pressure ranging from 0 to 5 bar abs.

8. The process as claimed in any claim 1, in which the distillation step c) is performed:

at a distillation column bottom temperature ranging from 150° C. to 200° C., and/or at a pressure of 1 bar abs; or at a distillation column bottom temperature ranging from 30° C. to 100° C., and/or at a pressure of 0.03 bar abs.

9. The process as claimed in claim 5, in which the alkali metal or alkaline-earth metal salt is chosen from the group consisting of MOH, $MOH.H_2O$, $MHCO_3$, $M_2CO_3$, MCl, $M(OH)_2$, $M(OH)_2.H_2O$, $M(HCO_3)_2$, $MCO_3$, $MCl_2$, and mixtures thereof.

10. The process as claimed in claim 5, in which step e) is performed at a temperature of less than or equal to 40° C.

11. The process as claimed in claim 1, also comprising a step g) of purification of the compound of formula (III).

* * * * *